(12) United States Patent
Olson et al.

(10) Patent No.: US 10,609,957 B2
(45) Date of Patent: Apr. 7, 2020

(54) VAPOR DELIVERY DEVICE

(71) Applicant: Funai Electric Co., Ltd., Osaka (JP)

(72) Inventors: Stephen T. Olson, Lexington, KY (US); Bruce D. Gibson, Lexington, KY (US); J. Glenn Edelen, Lexington, KY (US)

(73) Assignee: Funai Electric Co., Ltd., Osaka (JP)

( * ) Notice: Subject to any disclaimer, the term of this patent is extended or adjusted under 35 U.S.C. 154(b) by 402 days.

(21) Appl. No.: 15/358,525

(22) Filed: Nov. 22, 2016

(65) Prior Publication Data

US 2018/0140012 A1   May 24, 2018

(51) Int. Cl.
| | | |
|---|---|---|
| *A24F 47/00* | (2020.01) | |
| *H05B 1/02* | (2006.01) | |
| *A61M 15/00* | (2006.01) | |
| *A61M 15/02* | (2006.01) | |

(52) U.S. Cl.
CPC ....... *A24F 47/008* (2013.01); *A61M 15/0065* (2013.01); *A61M 15/025* (2014.02); *H05B 1/0244* (2013.01); *A61M 2210/0625* (2013.01); *H05B 2203/021* (2013.01)

(58) Field of Classification Search
CPC .............. A24F 47/008; H05B 1/0244; H05B 2203/021; A61M 15/0065; A61M 2210/0625; A61M 15/025
USPC ........................................................ 392/395
See application file for complete search history.

(56) References Cited

U.S. PATENT DOCUMENTS

| | | | |
|---|---|---|---|
| 3,607,668 A * | 9/1971 | Williamson | C02F 1/04 203/11 |
| 5,631,675 A | 5/1997 | Futagawa | |
| 5,657,060 A | 8/1997 | Sekiya | |
| 6,254,213 B1 | 7/2001 | Ishikawa | |
| 7,131,599 B2 | 11/2006 | Katase | |
| 7,398,778 B2 * | 7/2008 | Kaiser | F24F 3/001 126/101 |
| 8,333,188 B2 | 12/2012 | Masada et al. | |
| 8,430,469 B2 | 4/2013 | Nakamura | |
| 9,682,330 B1 * | 6/2017 | Sherry | B01D 1/30 |
| 2004/0039355 A1 | 2/2004 | Gonzalez | |
| 2006/0077217 A1 | 4/2006 | Yang et al. | |
| 2010/0157585 A1 * | 6/2010 | Diekmann | F21S 6/002 362/228 |
| 2012/0143152 A1 * | 6/2012 | Hunter | A61B 5/0059 604/298 |
| 2013/0286068 A1 | 10/2013 | Itaya | |
| 2016/0324212 A1 | 11/2016 | Cameron | |

* cited by examiner

*Primary Examiner* — Dana Ross
*Assistant Examiner* — Kuangyue Chen
(74) *Attorney, Agent, or Firm* — Luedeka Neely Group, P.C.; Rick Barnes; David LaRose

(57) ABSTRACT

A vapor delivery device having a reservoir for containing an amount of fluid. An ejector receives the fluid, and a controller fires the ejector to express a given dosage of the fluid through a number of nozzles in the ejector into an airstream at a firing frequency and for a firing duration. As the amount of the fluid within the reservoir decreases, the controller also at least one of reduces the firing frequency of the ejector, increases the number of nozzles, and increases the firing duration.

19 Claims, 2 Drawing Sheets

VAPOR DELIVERY DEVICE

FIELD

This invention relates to the field of vapor delivery devices. More particularly, this invention relates to controlling the flow of a source liquid through a vapor delivery device.

INTRODUCTION

Vapor delivery devices convert small doses of a liquid source to a vapor, which is then entrained in an airstream and drawn in by a user, such as into their lungs by breathing in the airstream. Vapor delivery devices could be used, for example, in devices that deliver medicine to a user, such as asthma inhalers. Vapor delivery devices could also be used for so-called e-cigarettes, also known as vaping devices.

The liquid source reservoir of some vapor delivery devices include a foam or felt material that wicks the liquid and acts as a delivery medium, and from which medium an ejector of some type draws the liquid for expression into a vaporizer. However, as the liquid is consumed, the medium is not able to provide transport of the liquid from the reservoir to the ejector at the same rate.

The end result is that the dose delivered by the vapor delivery device tends to change with time. At the start of the service life of the vapor delivery device, when the liquid source reservoir is relatively full, the dose tends to be at a relatively high level. However, at the end of the service life of the vapor delivery device, when the liquid source reservoir is relatively empty, the dose tends to be at a relatively low level. At points in between, the dose tends to vary according to at least the level of the liquid source reservoir, if not other additional factors.

While this situation is unsatisfactory in even casual applications such as vaping devices, it can be completely unacceptable—and potentially even life-threatening—in other more critical applications.

What is needed, therefore, is a vapor delivery device that reduces conditions such as those described above, at least in part.

SUMMARY

The above and other needs are met by a vapor delivery device having a reservoir for containing an amount of fluid. An ejector receives the fluid, and a controller fires the ejector to express a given dosage of the fluid through a number of nozzles in the ejector into an airstream at a firing frequency and for a firing duration. As the amount of the fluid within the reservoir decreases, the controller adjusts at least one of the firing frequency of the ejector, the number of nozzles, and the firing duration.

In some embodiments, the controller, when reducing the firing frequency of the ejector, also increases the number of nozzles used to express the fluid into the airstream, and thereby maintains the given dosage of the fluid. In some embodiments, the controller, when reducing the firing frequency of the ejector, also increases the firing duration used to express the fluid into the airstream, and thereby maintains the given dosage of the fluid.

In some embodiments, a power supply energizes the controller and the ejector. In some embodiments, the power supply is a battery. In some embodiments, a flash heater receives and evaporates into the airstream the fluid expressed by the ejector. In some embodiments, the flash heater is at least one of a wire, strip, and grid, energized by a power supply, which in some embodiments, is a battery. In some embodiments, the ejector includes a plurality of channels that receive the fluid and communicate the fluid to bubble chambers, where the fluid is energized by a plurality of at least one of resistance heating pads and piezoelectric devices, and is thereby expressed through a matrix of nozzles. In some embodiments, a medium receives the fluid from the reservoir and communicates the fluid to the ejector.

DRAWINGS

Further advantages of the invention are apparent by reference to the detailed description when considered in conjunction with the figure, which is not to scale so as to more clearly show the details, wherein like reference numbers indicate like elements, and wherein.

DESCRIPTION

General Overview

Figure 1:
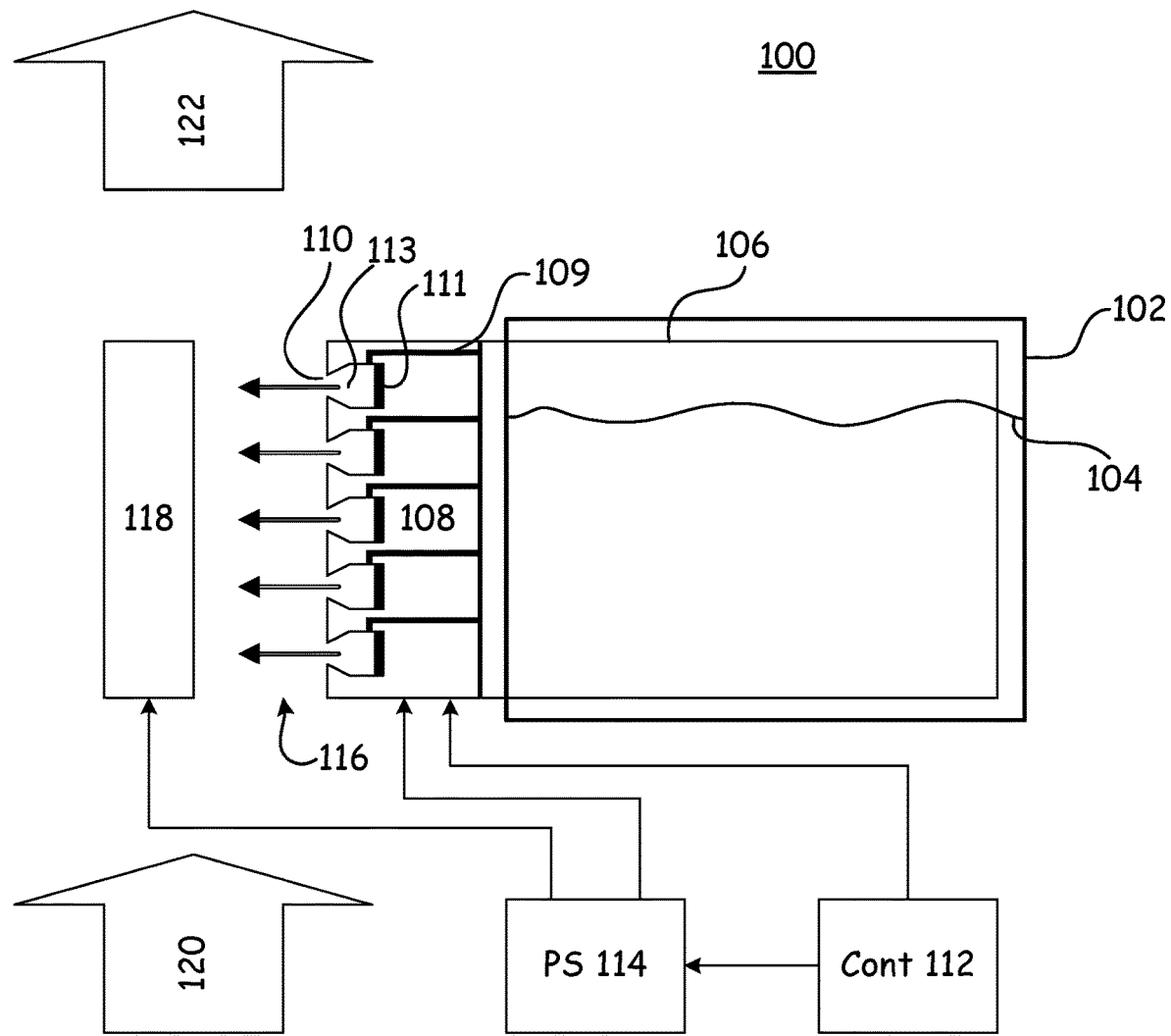
FIG. 1 depicts a functional block diagram of a vapor delivery device according to an embodiment of the present invention.

With reference now to FIG. 1, there is depicted a vapor delivery device 100 according to an embodiment of the present invention. In the embodiment depicted in the figure, a reservoir 102 contains a fluid 104 to be delivered as a vapor 122 by the vapor delivery device 100. The liquid 104 is communicated from the reservoir 102 such as by a medium 106, which in some embodiments is comprised of one or more materials that wick fluid, such as cloth, paper, felt, mat, web, and natural or man-made fibers.

The medium 106 can, in various embodiment, be disposed at an opening in the reservoir 102, or can substantially fill the reservoir 102. By filling substantially the entirety of the reservoir 102, the medium 106 tends to enable the vapor delivery device 100 to be used at any angle, as it is in constant contact with any remaining amount of the fluid 104, and is able to wick it do a desired location, as described below. Regardless of the exact configuration of the medium 106 in relation to the reservoir 102, the medium 106, in some embodiments, communicates the fluid 104 to an ejector 108.

The ejector 108, in the embodiment as depicted, receives the fluid 104 from the medium 106, and expresses it in one or more forms such as small droplets, a mist, or an aerosol 116. In some embodiments the expressed fluid 116 impinges upon a flash heater 118, such as one or more of a heated metal strip, wire, or grid, where it is absorbed by an air stream 120 that is flowing past the flash heater 118, becoming the vapor stream 122. In some embodiments the expressed fluid 116 is sufficiently finely expressed such that it is essentially vaporized within the incoming airstream 120, and no flash heater 118 is required to produce the vapor stream 122. Such design considerations can be determined, for example, by the viscosity and volatility of the fluid 104 to be used with the vapor delivery device 100.

A power supply 114, such as a battery, provides power to the flash heater 118 (if present) so that it can vaporize the expressed fluid 116, and also provides power to the ejector 108 so that it can eject the fluid 104 received from the medium 106. A controller 112 controls the operation of the components, such as the ejector 108 and the flash heater 118. The controller 112 can also track the operation of the vapor delivery device 100, such as by tracking the usage of the fluid 104 from the reservoir 102.

In some embodiments the ejector 108 is a device similar to an ink jet print head, where a matrix of nozzles 110 are used to express the fluid 104 as small droplets from the ejector 108. In one such embodiment, a plurality of small channels 109 receive the fluid 104 on one side of the ejector 108, communicate the fluid 104 to bubble chambers 113 in the ejector 108, where it is energized such as by one or more of resistance heating pads or piezoelectric devices 111, and is thereby expressed through the nozzles 110.

Specific Embodiment

There is now given a description of a more specific embodiment, where the vapor delivery device 100 is a vaping device, such as might be used as an e-cigarette. It is appreciated that other vapor delivery devices are still contemplated herein, even though this more specific embodiment is provided.

The fluid 104 used in a vaping application consists of a mixture of liquids that is mostly propylene glycol, water, and other additives such as flavorings to enhance taste and smell. These fluids 104 when combined have a viscosity in the range of about fifty centipoise to about one hundred centipoise at about twenty-five centigrade. Fluids 104 in this range of viscosity refill the ejector 108 (which is in a form similar to an ink jet print head as described above) in such a way as to limit the ejection frequency to less than about ten kilohertz, and in some embodiments to less than about four kilohertz.

Such a vaping device 100, when used for the first time, might have a back pressure within the reservoir 102 of less than about ten centimeters of water column (cmWc), at which pressure the ejector 108 refills completely, such that the drop 116 volume per fire is 100% of the intended volume per fire. As the vaping device 100 dispenses fluid 104 over time with continued use, the back pressure in the reservoir 104 begins to increase. As the ejector 108 is fired, the ejector 108 will not refill to 100% of design intent, because of the increased back pressure, and the delivered dose therefore decreases due to a lower drop 116 volume per fire, unless compensated for.

The vapor delivery device 100 as described in this embodiment uses a drop 116 counting module within the controller 112 to predict the change in back pressure in the reservoir 102, and the associated change in drop 116 volume as the device 100 is used, and fluid 104 is consumed from the reservoir 102. This is implemented, in one embodiment, by the controller 112 merely counting the number of nozzles 110 that are fired with each instruction to fire the ejector 108, and the number of times the ejector 108 is fired, and tracking the total number of drops of liquid 116 that have been expressed. As the number of drops 116 increases over time, at least a correlation with a commensurate decrease in the volume of fluid 104 remaining within the reservoir 102 can be accounted for.

In some embodiments, this management system as implanted by the controller 112 reduces the jetting frequency of the ejector 108 as the count of ejected drops 116 increases. In a first embodiment, the total ejection time is increased to compensate for the lower ejection frequency, so as to maintain the dose within the vapor stream 122. In a second embodiment, the number of nozzles 110 used by the ejector 108 upon each instruction to fire is increased as fluid 104 is drained and the jetting frequency is decreased.

In this manner, reducing the frequency of the jetting of the ejector 108 allows the medium 106 a greater length of time in which to communicate the fluid 104 to the ejector 108 as the amount of fluid 104 within the reservoir 102 decreases. And then at least one of either ejecting for a longer period of time once the ejector 108 fires, or using more of the nozzles 110 for a given firing of the ejector 108, compensates for the reduced frequency of firing. In some embodiments, the frequency is not reduced, but instead the jetting time or number of nozzles 110 used is increased to compensate for the increased back pressure. In this manner, the overall amount of fluid 116 expressed by the ejector 108 for a given volume of air in the stream 120 is maintained, and the dosage of the fluid 104 within the vapor 122 is better maintained.

In one embodiment, not all of the nozzles 110 are used when the reservoir 102 is relatively full, so that the dosage 122 can be maintained as the jetting frequency is decreased over time. In some embodiments, the utilization of the nozzles 110 is managed by the controller 112 by distributing usage continuously over the entire set of nozzles 110 available, and not just using a single subset of nozzles 110, and then adding a fixed set of nozzles 110 as the jetting frequency is reduced. Leaving a subset of nozzles 110 unused from the onset of usage tends to leave aged fluid 104 in the nozzles 110, and could lead to clogged nozzles 110.

Any of a number of approaches for nozzle 110 usage could be implemented in various embodiments, including a random selection of nozzles 110 up to the total number of nozzles 110 needed for the matching jetting frequency. As the reservoir 102 empties, and the back pressure approaches a design maximum (for example), the dot counter within the controller 112 prescribes the lowest jetting frequency and the management system prescribes that all nozzles 110 are utilized to maintain dose (for example). Eventually, the reservoir 102 is empty of fluid 104.

Method

Figure 2:
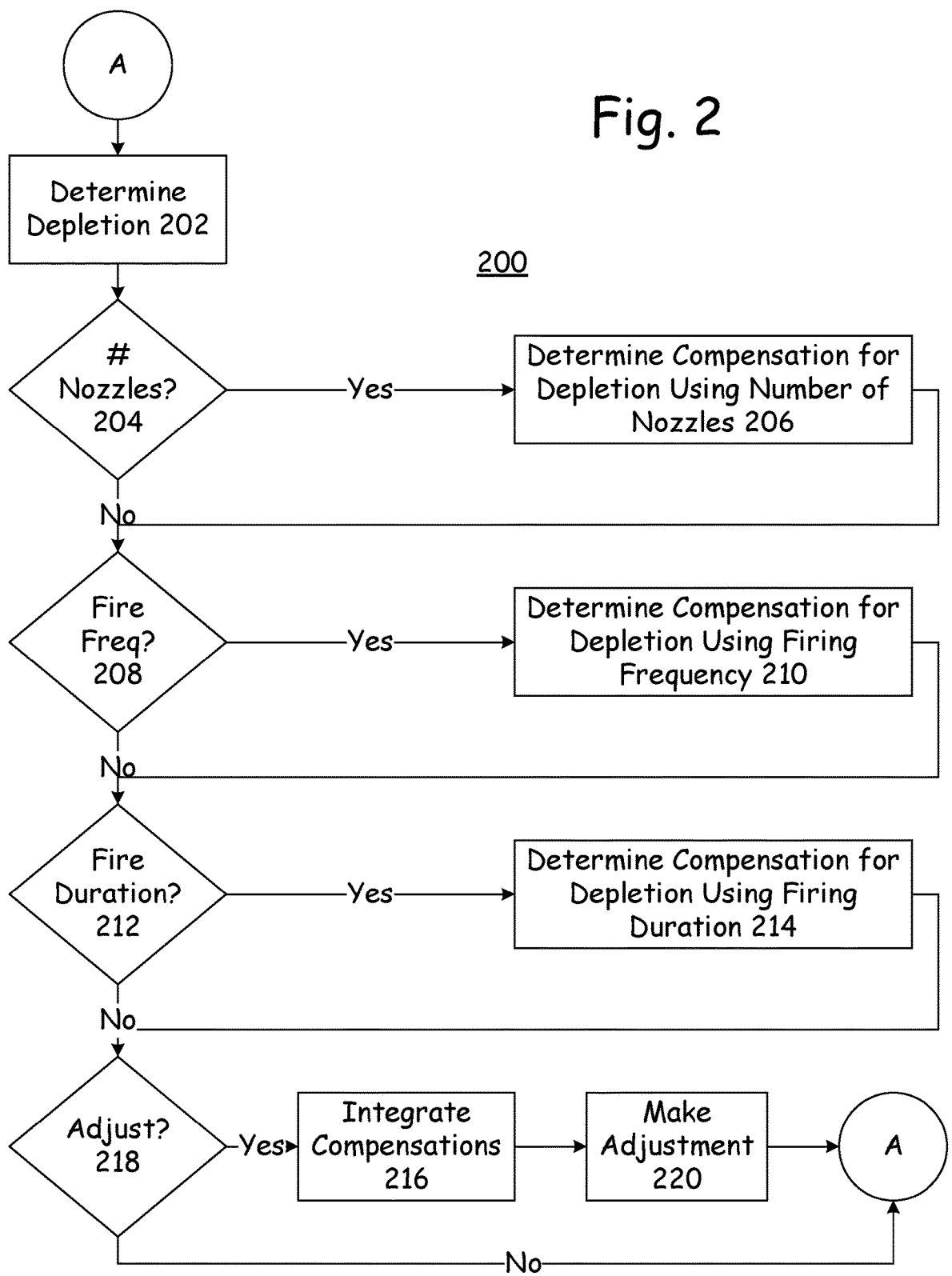
FIG. 2 depicts a flow chart of a method according to an embodiment of the present invention.

With reference now to FIG. 2, there is depicted a flow chart of a method 200 according to an embodiment of the present invention. Starting at entry point A, the method 200 falls to block 202, where the depletion of the reservoir 102 is determined. As introduced above, the depletion can be determined according to a variety of different methods, such as direct measurement of the amount of fluid 104 in the reservoir 102, measurement of the pressure within the reservoir 102, or counting the number of drops of fluid 104 that have been expressed by the ejector 108.

The method 200 then falls through a number of decision blocks 204, 208, and 212, where it is decided whether or not to determine compensations for the reduction in fluid 104 in the reservoir 102. For example, in block 204, the method 200 decides whether to determine a compensation for fluid 104 depletion in the reservoir 102 by adjusting the number of nozzles 110 through which the fluid 104 is expressed, as given in block 206.

Similarly, in block 208, the method 200 decides whether to determine a compensation for fluid 104 depletion in the reservoir 102 by adjusting the firing frequency of the ejector 108 through which the fluid 104 is expressed, as given in block 210. Finally, in block 212, the method 200 decides whether to determine a compensation for fluid 104 depletion in the reservoir 102 by adjusting the fire duration of the nozzles 110 through which the fluid 104 is expressed, as given in block 214.

In each case, the method 200 can decide whether or not to make one or more of these determinations, based upon criteria such as one or more of user input, preset programming, fluid 104 level within the reservoir 102, fluid 104 type, and so forth.

The system 100 decides whether to make the adjustments as determined by modules of 206, 210, and 214, as given in block 218. If the system 100 decides to not make the adjustments at this time, then the method returns to the entry point A for continued analysis of the system 100.

In block 216, the method 200 determines whether to integrate the compensations that are determined in one or more of blocks 206, 210, and 214. For example, it might be advantageous at some points in the process to make the compensation using the firing frequency and not the number of nozzles 110, whereas at another point in the process it might be advantageous to make the compensation using a combination of the number of nozzles 110 and the firing duration. These decisions are made in some embodiments by means of one or more of user input, preset programming, fluid 104 level within the reservoir 102, fluid 104 type, and so forth.

Once the integration has been made, as desired, then the one or more adjustments are made as given in block 220, and the method 200 then reenters to A for continued analysis of the system 100.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A vapor delivery device, comprising:
 a reservoir for containing an amount of fluid,
 an ejector for receiving the fluid,
 a controller adapted to fire the ejector to express a given dosage of the fluid through a number of nozzles in the ejector into an airstream at a firing frequency and for a firing duration, the controller having a counter for tracking the amount of the fluid, wherein as the amount of the fluid within the reservoir changes, the controller makes an adjustment to at least one of the firing frequency of the ejector, the number of nozzles, and the firing duration to thereby maintain the given dosage of fluid;
 a flash heater for receiving the fluid expressed by the ejector and evaporating the fluid into the airstream as a vapor; and
 a power supply for energizing the controller, the ejector, and the flash heater.

2. The vapor delivery device of claim 1, wherein the controller, when reducing the firing frequency of the ejector, also increases the number of nozzles used to express the fluid into the airstream, and thereby maintains the given dosage of the fluid.

3. The vapor delivery device of claim 1, wherein the controller, when reducing the firing frequency of the ejector, also increases the firing duration used to express the fluid into the airstream, and thereby maintains the given dosage of the fluid.

4. The vapor delivery device of claim 1, wherein the power supply is a battery.

5. The vapor delivery device of claim 1, wherein the flash heater is at least one of a wire, strip, and grid.

6. The vapor delivery device of claim 1, wherein the ejector comprises a plurality of channels that receive the fluid and communicate the fluid to bubble chambers, where the fluid is energized by a plurality of at least one of resistance heating pads and piezoelectric devices, and is thereby expressed through a matrix of nozzles.

7. The vapor delivery device of claim 1, further comprising a medium for receiving the fluid from the reservoir and communicating the fluid to the ejector.

8. A method of maintaining a given dosage of fluid, the method comprising the steps of:
 storing an amount of fluid in a reservoir,
 providing the fluid from the reservoir to an ejector, thereby depleting fluid within the reservoir,
 tracking the amount of the fluid,
 expressing the fluid into an airstream through a number of nozzles in the ejector at a firing frequency and for a firing duration, and
 as the amount fluid in the reservoir is depleted, adjusting at least one of the firing frequency, the number of nozzles, and the firing duration to maintain the given dosage of fluid, based at least in part on the amount of the fluid remaining in the reservoir.

9. The method of claim 8, wherein a controller reduces the firing frequency of the ejector and increases the number of nozzles used to express the fluid into the airstream to thereby maintain the given dosage of the fluid.

10. The method of claim 8, wherein a controller reduces the firing frequency of the ejector and increases the firing duration used to express the fluid into the airstream to thereby maintain the given dosage of the fluid.

11. The method of claim 8, further comprising receiving and evaporating into the airstream the fluid expressed by the ejector by use of a flash heater.

12. The method of claim 11, further comprising energizing the flash heater by use of a battery.

13. The method of claim 8, further comprising expressing the fluid from a matrix of bubble chambers and nozzles by energizing a plurality of at least one of resistance heating pads and piezoelectric devices in the bubble chambers.

14. The method of claim 8, further comprising delivering fluid to the ejector from the reservoir by use of a fluid delivery medium.

15. A method of expressing a given dosage of fluid, comprising the steps of:
 storing an amount of fluid in a reservoir,
 providing the fluid from the reservoir to an ejector, thereby depleting the amount of the fluid within the reservoir,
 expressing the fluid into an airstream through a number of nozzles in the ejector at a firing frequency and for a firing duration,
 receiving and evaporating into the airstream the fluid expressed by the ejector by use of a flash heater, and
 as the amount of the fluid in the reservoir changes, adjusting one or more of the firing frequency of the ejector, the number of nozzles, and the firing duration to maintain the given dosage of fluid.

16. The method of claim 15, wherein a controller reduces the firing frequency of the ejector and increases the number of nozzles used to express the fluid into the airstream to thereby maintain the given dosage of the fluid.

17. The method of claim 15, wherein a controller reduces the firing frequency of the ejector and increases the firing duration used to express the fluid into the airstream to thereby maintains the given dosage of the fluid.

18. The method of claim 15, wherein a plurality of at least one of resistance heating pads and piezoelectric devices expresses the fluid from the ejector into the airstream.

19. The method of claim 16, wherein a power supply energizes the controller, the ejector and the flash heater.

* * * * *